United States Patent
Le Thiesse et al.

(10) Patent No.: US 8,962,884 B2
(45) Date of Patent: Feb. 24, 2015

(54) METHOD FOR PREPARING A COMPLEX OF AN ACID AND A METAL

(75) Inventors: Jean-Claude Le Thiesse, Saint-Etienne (FR); Patrick Rey, Lyons (FR); Vivien Henryon, Lyons (FR)

(73) Assignee: Adisseo Ireland Limited, Dublin (IE)

( * ) Notice: Subject to any disclaimer, the term of this patent is extended or adjusted under 35 U.S.C. 154(b) by 0 days.

(21) Appl. No.: 13/821,338

(22) PCT Filed: Sep. 21, 2011

(86) PCT No.: PCT/FR2011/052171
§ 371 (c)(1),
(2), (4) Date: Mar. 7, 2013

(87) PCT Pub. No.: WO2012/038660
PCT Pub. Date: Mar. 29, 2012

(65) Prior Publication Data
US 2013/0172617 A1    Jul. 4, 2013

(30) Foreign Application Priority Data
Sep. 22, 2010 (FR) ...................................... 10 57605

(51) Int. Cl.
C07C 319/20 (2006.01)
B29B 9/00 (2006.01)
B22D 11/01 (2006.01)
C07C 51/41 (2006.01)

(52) U.S. Cl.
CPC ............. *C07C 319/20* (2013.01); *C07C 51/412* (2013.01)
USPC ............................... 562/581; 254/141; 254/15

(58) Field of Classification Search
CPC combination set(s) only.
See application file for complete search history.

(56) References Cited

U.S. PATENT DOCUMENTS

2007/0227399 A1    10/2007    Abou-Nemeh

FOREIGN PATENT DOCUMENTS

| DE | 19707380 A1 | 8/1998 |
|---|---|---|
| EP | 0049057 A1 | 4/1982 |
| EP | 1260493 A1 | 11/2002 |

OTHER PUBLICATIONS

Todd "Mixing of Highly Viscous Media", Ullmann's Encyclopedia of Industrial Chemistry, 2000, p. 387-401.*

* cited by examiner

*Primary Examiner* — Jafar Parsa
*Assistant Examiner* — Amy C Bonaparte
(74) *Attorney, Agent, or Firm* — Porzio, Bromberg & Newman, P.C.

(57) ABSTRACT

The invention concerns a method for preparing a complex of an acid chosen from among methionine, 2-hydroxy-4-methylthiobutanoic acid (HMTBA) and lactic acid, and of at least one metal, starting from said acid and a mineral metal source, wherein the acid is caused to react with the mineral metal source in an extruder.

18 Claims, 1 Drawing Sheet

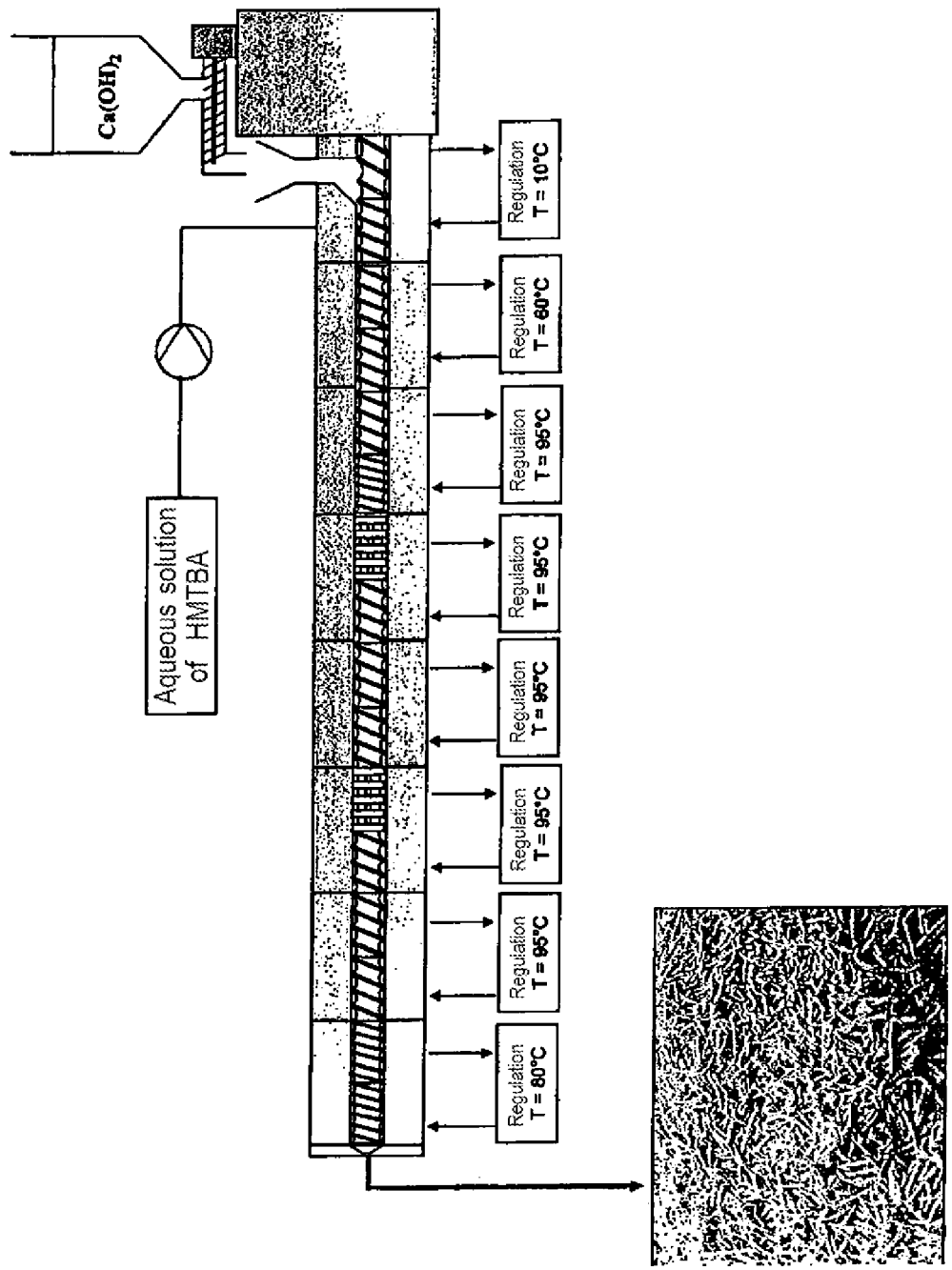

METHOD FOR PREPARING A COMPLEX OF AN ACID AND A METAL

CROSS REFERENCE TO RELATED APPLICATION

This is a National Stage of International Application No. PCT/PR2011/052171, filed 21 Sep. 2011, which claims the benefit of Application Ser. No. 10/57605, filed in France on 22 Sep. 2010, the disclosures of which Applications are incorporated by reference herein.

The invention concerns a method for preparing a complex of an acid and at least one metal. More precisely, this method pertains to the manufacture of a metal complex of an acid substituted at alpha position of the carboxylic group by an amino or hydroxyl group. The method of the invention finds particular interest in the obtaining of a metal complex of an acid chosen from among methionine, 2-hydroxy-4-methylthiobutanoic acid (HMTBA) and lactic acid.

Since the carbon carrying the amino or hydroxyl group and the carboxylic group is asymmetric, by acid is meant herein each of the isomers thereof, L- or D-, or the mixtures thereof and in particular the racemic.

Methionine, an essential amino acid, and HMTBA an analogue of methionine, find extensively wide applications in man as food supplement or medication, and for animal nutrition. Their metal salts, for example the calcium or zinc salts in solid form, may be preferred. The latter can also be used to compensate for deficiencies in elements or trace elements. The best known HMTBA salt is the dicalcium salt comprising two moles of HMTBA equivalent per mole of calcium meeting the formula $(HMTBA)_2Ca$.

From EP 140865A a method is known for preparing calcium salts of HMTBA, consisting of more than two and less than ten moles of HMTBA equivalent per mole of calcium. These salts are obtained by causing HMTBA to react with a source of calcium chosen from among calcium oxide (CaO), calcium hydroxide $(Ca(OH)_2)$, calcium carbonate $(CaCO_3)$ and a salt of HMTBA e.g. the salt $(HMTBA)_2Ca$. HMBTA is generally in highly concentrated aqueous solution, with which the calcium source is mixed, and the reaction medium thus obtained is dried at a temperature of the order of 70° C. The reaction medium of HMTBA with the calcium source is highly viscous however and tacky; it is therefore very difficult to homogenize in mixers or reactors equipped with conventional agitation systems, and at the end of the reaction it is necessary to conduct in situ drying in order to be able to empty the reactor. Recycling of the calcium salt of HMTBA, for example the $(HMTBA)_2Ca$ salt, towards the calcium source before placing it in contact with HMTBA provides an improvement in the consistency of the reaction medium and facilitates the implementation of the method. However, as taught by U.S. Pat. No. 4,335,257, this improvement is observed for a weight proportion of at least 20% of the said salt relative to the reaction medium, and to arrive at an acceptable consistency it may be necessary for this proportion to reach 80% of the reaction medium. Said recycling rate of the finished product in the reaction mixture considerably reduces the productivity of an industrial installation and necessitates large over-sizing of the mixer/reactor for a desired production capacity.

WO03/011822A2 proposes a method for preparing organic acid salts, in particular calcium salts, from a said organic acid and calcium hydroxide and/or calcium oxide in which the organic acid is deposited on an inert substrate before adding the calcium source thereto. Despite the presence of this substrate, it is essential to introduce the two reagents in successive additions to allow drying of the reaction medium between two additions. This operating mode substantially prolongs the residence time in the mixer and also necessitates large over-sizing of this said mixer for a given production capacity. In addition, the inert substrate is found in the end dry product in which it represents 30 to 50% by weight of the total weight, which reduces the content of active matter accordingly and thereby generates additional costs for use of the product (storage, transport, dosage . . . ).

It follows from the prior art that the preparation of organic acid salts and in particular of HMTBA necessitates the recourse to a stratagem, generally the addition of a compound to the reaction medium in order to improve its consistency and allow the handling thereof.

The authors of the present invention have developed a simple method for preparing one or more salts of HMTBA with which it is possible to bypass the above-mentioned obstacles, without however having recourse to a substrate or other excipient.

Therefore, there is provided according to the invention a method for preparing a complex of an acid chosen from among methionine, 2-hydroxy-4-methylthiobutanoic acid (HMTBA) and lactic acid, and of at least one metal, starting from the said acid and a mineral metal source, a method according to which the acid and the mineral metal source are caused to react in a extruder.

The authors have discovered that the kinetics of the aforementioned reaction are perfectly compatible with this continuous technology, despite the residence time which does not exceed a few minutes, even in general less than one minute. This technology effectively allows maximizing of the intensity of the mixing of the reagents, and the obtaining of a perfectly homogeneous mixture despite the high viscosity. Therefore, the yield of the reaction is excellent and the salts formed are practically free of residual oligomers. In addition, the self-cleaning nature of the extruder screws allows the reaction medium to be easily conveyed despite its highly tacky nature without the need to have recourse to any inert substrate whatsoever or to any recycling of the end product towards the feed of the extruder.

This method does not have recourse to any prior treatment of the reagents, acid and metal source, or the mixture thereof. In particular, it does not require the addition of any solvent, or of any other additive or recycling of the end product and nor does it require preheating of the reagents. This method therefore dispenses with any steps for handling the reagents and the mixture thereof which directly forms the reaction medium. Only an addition of water may be needed for feeding the extruder if the two reagents do not contain sufficient water in their initial form; this is particularly the case when the two reagents are solids. The quantity of added water is calculated such that the total quantity of water used in the extruder is between 5 and 20% preferably between 10 and 15%.

Before going into further details of the description of the method according to the invention, a definition of some of the terms used is given.

By metal according to the invention is meant any element in the periodic table capable of forming one or more cations and belonging to the groups of metals, in particular alkaline, alkaline-earth and transition metals and metalloids.

By complex according to the invention is meant a compound comprising at least one metal atom and at least one molecule of an acid such as defined above, in which at least one atom of the acid molecule is linked to the metal atom or to the metal atoms for preparing mixed salts via a chemical bond or a chemical interaction. As an illustration, a said bond or bonds or a said chemical interaction or interactions are chosen from among ion bonds, coordination bonds, Van der Waals bonds . . . . A complex according to the invention may comprise several of the above described compounds. As an illustration, a complex of the invention may be represented by the formula $(Acid)_n X_p Y_p$ where X and Y each independently represent a metal, n varies from 1 to 10, and p and q vary from 0 to 10, the sum of p and q varying from 1 to 10. The present invention is more particularly illustrated by the preparation of salts, but the method of the invention applies to any complex such as defined above.

The expression <<practically free of oligomers>>relating to the complex obtained according to the invention, means that the method generally does not lead to a content of residual oligomers of more than 0.4% even no more than 0.1%. This is the content observed when the acid is HMTBA.

Various devices have the capacity of providing the mixing conditions for the reaction medium according to the invention. As an example, mention may be made of twin-screw, co-rotating or counter-rotating extruders, single screw mixers. These technologies are characterized by a relatively short residence time, no more than a few minutes, often less than one minute. Consequently, the quantity of product contained in the apparatus is small on account of the mechanical energy dissipated and the available heat exchange surface. The result is mechanical treatment of the reaction medium during which mass and heat transfers are maximized.

This leads to optimisation of the reaction, the conversion rate of the reagents generally reaching 99%, and to obtaining of a complex which can be directly engaged in a fractionation and/or drying step without requiring additional handling.

The use of a twin-screw extruder is preferred. The method is advantageously carried out in a co-rotating twin-screw extruder i.e. whose screws rotate in the same direction. The reagents are fed into the extruder and are mixed to form the reaction mixture and produce the complex therein. The adapting of the characteristics of the said device evidently forms part of the general knowledge of persons skilled in the art. In particular, the profile of the screw is designed so as to ensure the three main desired functions: mixing of the reagents, conveying and intensive mixing of the reaction medium. Advantageously several mixing zones are alternated with conveying zones. The jacket of the extruder is preferably equipped with several heating sleeves which allow the temperature to be varied along the extruder. Therefore the reaction conditions, shear rate and mass temperature are optimized along the extruder in accordance with the state of progress of the reaction. These optimal conditions evidently depend upon the chemical nature of the reagents and the desired complex. The determination thereof follows from the general skill of those skilled in the art.

At its end part the extruder can be fitted with a die. In this case, the complex is preferably expelled from the extruder in the form of rods that are non-tacky and can be used directly or if necessary easily transported towards a drying step. This forming of the complex allows the use of any type of dryer in particular convective dryers whose energy yield is much higher than conductive drying which is imposed by prior art methods.

The feed rates of the two reagents, acid and metal source, are regulated in relation to their respective chemical nature and the type of desired complex. If necessary, water is simultaneously added so that the total quantity of water injected into the extruder allows the formation of a paste. Typically, the total quantity of water represents between 10 and 15% of the total mass. If the intended application so requires, it is also possible to add small quantities of excipients, e.g. starch possibly reaching 15%, preferably from 100 ppm to 5% of the total mass.

The method advantageously meets the following additional characteristics which are to be considered alone or in any technical combination with each other:

the metal is chosen from among Li, Na, K, Mg, Ca Mn, Fe, Co, Ni, Cu, Zn, Pt.

the mineral metal source is chosen from among metallic hydroxides, metallic hydroxide milks, metallic oxides and the corresponding metallic carbonates whether or not of natural origin; when it is of natural origin, it can be chosen from among shells, ores and rocks.

a calcium complex of HMTBA is preferably obtained according to the invention; when the metal is calcium the calcium source is advantageously chosen from among lime, milk of lime, slaked lime, calcium hydrogen carbonate and calcium carbonate; when it is of natural origin, it can be chosen from among oyster shell, snail shell dolomite; preferably the calcium source is $Ca(OH)_2$, a complex of a metal chosen from among zinc, copper and manganese, methionine or HMTBA is also a preferred complex of the invention, the metal source is then advantageously chosen from among zinc/copper/manganese oxide, zinc/copper/manganese hydroxide, an aqueous solution zinc/copper/manganese hydroxide and zinc/copper/manganese carbonate.

the acid/metal source weight ratio is determined by those skilled in the art in relation to the desired complex, the reaction temperature is lower than 150° C., preferably it varies between 60 and 120° C., more preferably from 80 to 95° C.

The complex thus obtained can be fractionated and/or dried, and may undergo an additional forming step for example to reach a determined particle size using spheronization for example.

If the managing of the production workshop so requires, the method of the invention may include recycling of the end product towards the feed to the extruder, for example of very fine particles generated in the downstream steps of the method. As indicated in the foregoing, this recycling is possible but not indispensable for the proper functioning the extruder taking into account the self-cleaning nature of the screws, and little recourse is had thereto.

The method according to the invention therefore has numerous advantages:

continuous process, reagents used without any pre-treatment, in particular no dilution or pre-heating, no recycling of the final product and no addition of essential additives, hence a flow to be treated that is equal to the actual production flow, conversion rate of the acid higher than 99% and content of residual oligomers less than 0.4%, forming when leaving the extruder, allowing convective drying, no excipient in the final product, hence a very high content of active material.

In addition to the ease of implementation of the method, all these advantages give rise to an economic advantage: minimized investment (number and size of the equipment), increased energy yield (intensive process, convective drying).

The invention is illustrated below in connection with the sole FIGURE and the following examples in which:

the FIGURE illustrates an extruder in which the method of the invention, in particular the one described in Example 1 is implemented, the examples describe the preparation of a calcium complex of HMTBA starting from HMTBA and slaked lime in a twin-screw extruder.

Evidently, the method of the invention is not restricted to the said implementation, and in particular it is fully adapted for forming other metal complexes of HMTBA and any metal complexes of methionine and lactic acid.

EXAMPLE 1

Internal Reference for the Record: AGT 49

In accordance with the FIGURE a co-rotating, twin-screw CLEXTRAL BC21 extruder equipped with 8 jackets, i.e. L/D=32 is fed with:
- 1.2 kg/h of GPR Rectapur slaked lime marketed by VWR, using a K-Tron gravimetric feeder,
- 5.0 kg/h of AT88 marketed by Adisseo, using a metering pump.

The two reagents are at ambient temperature when added to the extruder. The temperature profile imposed along the extruder is described in the FIGURE and allows the reaction mass to be held at:
- T<60° C. in the mixing zone of the 2 reagents,
- T=95° C. in the reaction zone,
- T=80° C. at the die, The screw rotating speed is 150 rpm.

The residence time in the extruder is estimated at 90 seconds.

The reaction mass is extruded though a 1-hole die having a diameter of 1.6 mm.

The extrudates obtained are dried for 12 hours in an oven at 60° C.; the residual moisture content is 0.5%.

HPLC analysis reveals a residual dimer content of less than 0.01%.

DSC analysis shows a single endothermal signal characteristic of the decomposition of the double salt (HMTBA)$_2$Ca: onset temperature of 257° C. and enthalpy of 270 J/g for a temperature rise of 2° C./mn. The absence of any signal in the temperature range of 120-140° C. proves that the product obtained is fully free of (HMTBA)$_4$Ca salt.

EXAMPLE 2

A co-rotating, twin-screw CLEXTRAL BC21 extruder equipped with 9 jackets, i.e. L/D=36, is fed with:
- 2.4 kg/h of GPR Rectapur slaked limed marketed by VWR, using a K-Tron gravimetric feeder,
- 10.0 kg/h of AT88 marketed by Adisseo, using a metering pump.

The two reagents are at ambient temperature when added to the extruder. The temperature profile imposed along the extruder allows the reaction mass to be held at:
- T<60° C. in the mixing zone of the 2 reagents,
- T=105° C. in the reaction zone,
- T=105° C. at the die.

The screw rotating speed is 250 rpm.

The residence time in the extruder is estimated at 50 seconds.

The reaction mass is extruded through a 7-hole die, the hole diameter being 1.2 mm. The extrudates obtained are dried for 4 hours in an oven at 60° C.; the residual moisture content is 1.5%.

HPLC analysis reveals a residual dimer content of less than 0.03%.

EXAMPLE 3

A co-rotating, twin-screw CLEXTRAL BC21 extruder equipped with 9 jackets, i.e. L/D=36, is fed with:
- 3.6 kg/h of GPR Rectapur slaked lime marketed by VWR, using a K-Tron gravimetric feeder,
- 15.0 kg/h of AT88 marketed by Adisseo, using a metering pump.

The two reagents are at ambient temperature when added to the extruder. The temperature profile imposed along the extruder allows the reaction mass to be held at:
- T<60° C. in the mixing zone of the 2 reagents,
- T=105° C. in the reaction zone,
- T=105° C. at the die.

The screw rotating speed is 450 rpm.

The residence time in the extruder is estimated at 25 seconds.

The reaction mass is extruded through a 12-hole die, the hole diameter being 0.8 mm The extrudates obtained are dried for 4 hours in an oven at 60° C.; the residual moisture content is 1.5%.

HPLC analysis shows a residual dimer content of less than 0.06%.

EXAMPLE 4

A co-rotating, twin-screw CLEXTRAL Evolum HT 53 D 101 extruder equipped with 10 jackets, i.e. L/D=40, is fed with:
- 19.4 kg/h of A2205 slaked lime marketed by Bonargent-Goyon using a K-Tron gravimetric feeder,
- 76.6 kg/h of AT88 marketed by Adisseo, using a metering pump.

The two reagents are at ambient temperature when added to the extruder. The temperature profile imposed along the extruder allows the reaction mass to be held at:
- T<60° C. in the mixing zone of the 2 reagents,
- T=110° C. in the reaction zone,
- T=80° C. at the die.

The screw rotating speed is 200 rpm.

The residence time in the extruder is estimated at 60 seconds.

The reaction mass is extruded through a 14-hole die, the hole diameter being 1.4 mm. The extrudates obtained are dried for 2 hours in a oven at 90° C.; the residual moisture content is 2.0%.

HPLC analysis reveals a residual dimer content of less than 0.09%.

The invention claimed is:

1. A method for preparing a complex of an acid chosen from among methionine, 2-hydroxy-4-methylthiobutanoic acid (HMTBA) and lactic acid, and of at least one metal, starting from the said acid and a mineral metal source, adding the acid and the mineral metal source to an extruder; and
reacting the acid with the mineral metal source in the extruder;
wherein the temperature is varied along with the extruder and the residence time in the extruder does not exceed 90 seconds.

2. The method according to claim 1, wherein the metal is selected from the group consisting of Li, Na, K, Mg, Ca, Mn, Fe, Co, Ni, Cu, Zn, and Pt.

3. The method according to claim 1, wherein the mineral metal source is selected from the group consisting of metallic hydroxides, metallic hydroxide milks, metallic oxides and corresponding metallic carbonates, whether or not of natural origin.

4. The method according to claim 3, wherein the mineral metal source is of natural origin and is selected from the group consisting of shells, ores and rocks.

5. The method according to claim 1, wherein the acid is 2-hydroxy-4-methylthiobutanoic acid (HMTBA) and the metal is calcium, the calcium source being selected from the group consisting of lime, milk of lime, slaked lime, calcium hydrogen carbonate and calcium carbonate.

6. The method according to claim 5 wherein the mineral metal source is selected from the group consisting of oyster shell, snail shell, and dolomite.

7. The method according to claim 5, wherein the calcium source is $Ca(OH)_2$.

8. The method according to claim 1, wherein the acid is methionine or 2-hydroxy-4-methylthiobutanoic acid (HMTBA) and the metal is selected from the group consisting of zinc, manganese and copper, the metal source being selected from the group consisting of oxide, hydroxide, aqueous hydroxide solution and the corresponding metal carbonate.

9. The method according to claim 1, wherein the extruder is selected from the group consisting of a single-screw mixer and a twin-screw extruder.

10. The method according to claim 1, wherein the reaction is conducted between 2-hydroxy-4-methylthiobutanoic acid (HMTBA) and $Ca(OH)_2$ in a twin-screw extruder.

11. The method according to claim 10, wherein the twin-screw extruder is co-rotating.

12. The method according to claim 1, wherein the reaction temperature is lower than 150° C.

13. The method according to claim 12, wherein the reaction temperature varies between 60 and 120° C.

14. The method according to claim 1, further comprising a fractionating and/or drying step of the complex obtained.

15. The method according to claim 14, wherein the fractionation is conducted by passing through a die or by grinding.

16. The method according to claim 1, further comprising a step of forming a particle size of the complex obtained.

17. The method according to claim 12, wherein the reaction temperature varies between between 80 and 95° C.

18. The method according to claim 16 wherein the particle size is obtained using spheronization.

* * * * *